US012690751B2

(12) United States Patent
Chen

(10) Patent No.: US 12,690,751 B2
(45) Date of Patent: Jul. 28, 2026

(54) ENDOSCOPE IMAGE CORRECTION SYSTEM AND METHOD

(71) Applicant: Chieh-Hsiao Chen, Taichung City (TW)

(72) Inventor: Chieh-Hsiao Chen, Taichung City (TW)

( * ) Notice: Subject to any disclaimer, the term of this patent is extended or adjusted under 35 U.S.C. 154(b) by 818 days.

(21) Appl. No.: 17/909,336

(22) PCT Filed: Mar. 8, 2021

(86) PCT No.: PCT/CN2021/079591
§ 371 (c)(1),
(2) Date: Sep. 2, 2022

(87) PCT Pub. No.: WO2021/180043
PCT Pub. Date: Sep. 16, 2021

(65) Prior Publication Data
US 2023/0079449 A1 Mar. 16, 2023

Related U.S. Application Data

(60) Provisional application No. 62/986,810, filed on Mar. 9, 2020.

(51) Int. Cl.
*G06K 9/00* (2022.01)
*A61B 1/005* (2006.01)
(Continued)

(52) U.S. Cl.
CPC .............. *A61B 1/005* (2013.01); *A61B 1/045* (2013.01); *G06T 7/80* (2017.01)

(58) Field of Classification Search
CPC .... G06T 7/80; G06T 7/70; G06T 2207/10068
See application file for complete search history.

(56) References Cited

U.S. PATENT DOCUMENTS

| | | | |
|---|---|---|---|
| 10,148,929 B2 | 12/2018 | Huang et al. | |
| 11,674,906 B1 * | 6/2023 | Olsson | H04N 23/6812 |
| | | | 348/84 |

(Continued)

FOREIGN PATENT DOCUMENTS

| | | |
|---|---|---|
| CN | 102207674 A | 10/2011 |
| CN | 102866573 A | 1/2013 |

(Continued)

OTHER PUBLICATIONS

The International Search Report and Written Opinion dated Jun. 7, 2021 from the International Application PCT/CN2021/079591.

*Primary Examiner* — Avinash Yentrapati
(74) *Attorney, Agent, or Firm* — Haverstock & Owens, A Law Corporation

(57) ABSTRACT

An endoscopic image correction system includes: an endoscopic image retrieving device for retrieving a first image at a first time and a second image at a second time, the first image being associated with a first image picture-taking angle and a first image display angle, and the second image being associated with a second image picture-taking angle; a processing device for determining a first angular difference between the first image picture-taking angle and the second image picture-taking angle, calculating a second image display angle according to the first image display angle and the first angular difference, and associating the second image display angle with the second image; and a display device for displaying the first image at the first image display angle and the second image at the second image display angle, wherein the processing device is communicatively connected to the endoscopic image retrieving device and the display device.

10 Claims, 7 Drawing Sheets

(51) Int. Cl.
    *A61B 1/045*         (2006.01)
    *G06T 7/80*          (2017.01)

(56)               References Cited

U.S. PATENT DOCUMENTS

| | | | |
|---|---|---|---|
| 2014/0198897 A1* | 7/2014 | Sakaguchi | A61B 6/502 |
| | | | 378/98.2 |
| 2014/0307053 A1 | 10/2014 | Huang et al. | |
| 2015/0119638 A1* | 4/2015 | Yu | A61B 90/30 |
| | | | 600/102 |
| 2018/0150929 A1* | 5/2018 | Pheiffer | G06T 3/14 |
| 2018/0300954 A1* | 10/2018 | Fu | G06T 15/205 |
| 2020/0352411 A1 | 11/2020 | Tojo et al. | |
| 2021/0240988 A1* | 8/2021 | Lim | G08B 21/02 |
| 2022/0222893 A1* | 7/2022 | Li | G06V 40/18 |
| 2023/0180996 A1* | 6/2023 | Dai | A61B 1/0005 |
| | | | 600/109 |

FOREIGN PATENT DOCUMENTS

| | | |
|---|---|---|
| CN | 104113684 A | 10/2014 |
| CN | 110720882 A | 1/2020 |
| JP | WO2019130390 | 7/2019 |

* cited by examiner

500

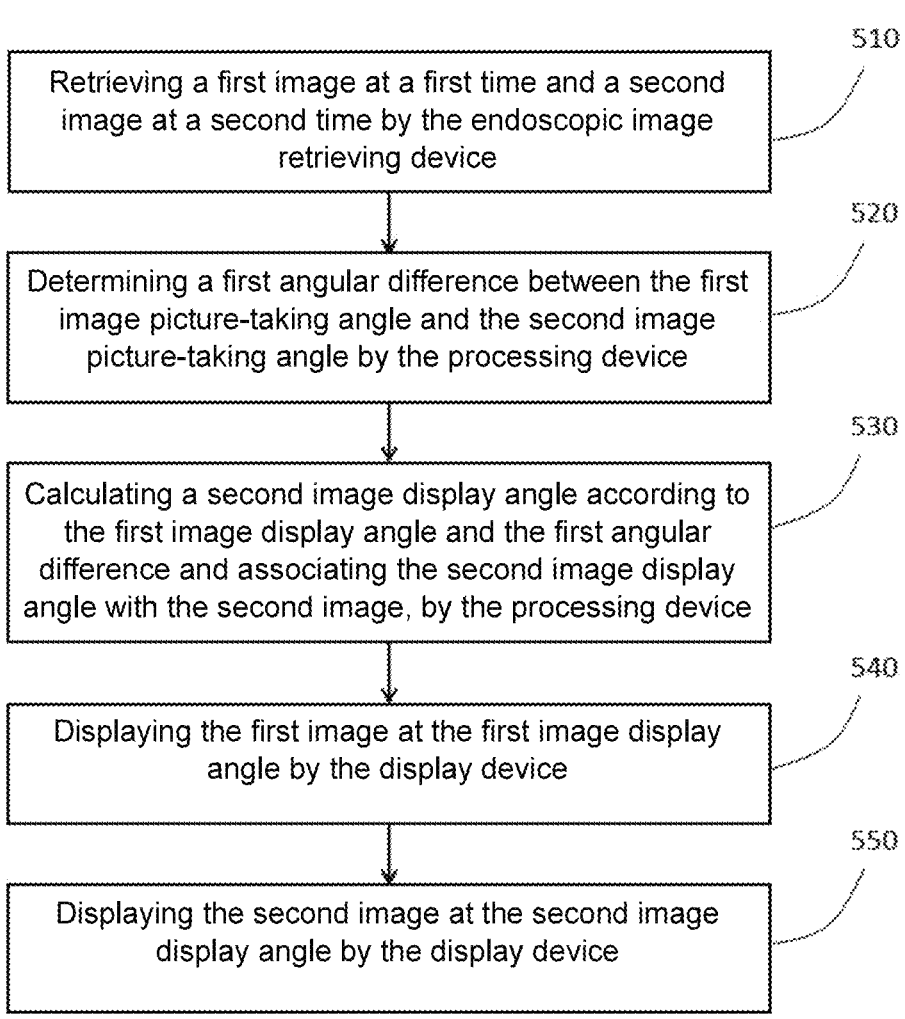

Retrieving a first image at a first time and a second image at a second time by the endoscopic image retrieving device — 510

Determining a first angular difference between the first image picture-taking angle and the second image picture-taking angle by the processing device — 520

Calculating a second image display angle according to the first image display angle and the first angular difference and associating the second image display angle with the second image, by the processing device — 530

Displaying the first image at the first image display angle by the display device — 540

Displaying the second image at the second image display angle by the display device — 550

FIG.5

ENDOSCOPE IMAGE CORRECTION SYSTEM AND METHOD

BACKGROUND OF THE INVENTION

Field of the Invention

The present disclosure relates to an endoscopic image correction system and method and, more particularly, to an endoscopic image correction system and method for use with medical endoscopic systems.

Description of the Prior Art

The movements (for example, the turning or rotation) of the cameras of existing conventional endoscopic systems inside the human body synchronize with the consequent rotations (i.e., consequent changes in the image display angle) of images displayed on the display screens of the endoscopic systems. As a result, persons operating the endoscopic systems are too confused to correctly determine the position and direction of the cameras, thereby adding to the difficulties in operation. In view of this, it is necessary to provide an endoscopic image correction system and method effective in keeping a fixed viewing angle at which images are displayed while the cameras of the endoscopic systems are moving inside the human body.

SUMMARY OF THE INVENTION

In view of the aforesaid drawbacks of the prior art, it is an objective of the disclosure to provide an endoscopic image correction system and method effective in keeping a fixed viewing angle at which images are displayed while the camera of the endoscopic system is moving inside the human body.

In order to achieve the above and other objectives, the disclosure provides an endoscopic image correction system, comprising: an endoscopic image retrieving device for retrieving a first image at a first time and a second image at a second time, the first image being associated with a first image picture-taking angle and a first image display angle, and the second image being associated with a second image picture-taking angle; a processing device for determining a first angular difference between the first image picture-taking angle and the second image picture-taking angle, calculating a second image display angle according to the first image display angle and the first angular difference, and associating the second image display angle with the second image; and a display device for displaying the first image at the first image display angle and the second image at the second image display angle, wherein the processing device is communicatively connected to the endoscopic image retrieving device and the display device.

In a preferred embodiment of the disclosure, the second image follows the first image.

In a preferred embodiment of the disclosure, a second angular difference is defined between the first image display angle and the second image display angle and is equal to the first angular difference.

In a preferred embodiment of the disclosure, the endoscopic image correction system further comprises a position sensor for sensing the first image picture-taking angle at the first time and sensing the second image picture-taking angle at the second time, with the position sensor being communicatively connected to the processing device.

In a preferred embodiment of the disclosure, the position sensor is a G-sensor.

In a preferred embodiment of the disclosure, the processing device determines the first angular difference according to the first image picture-taking angle and the second image picture-taking angle.

In a preferred embodiment of the disclosure, the first image has a first feature region at a first position, and the second image has a second feature region at a second position, with the second feature region corresponding in position to the first feature region, wherein the processing device determines the first angular difference according to the first position and the second position.

In order to achieve the above and other objectives, the disclosure further provides an endoscopic image correction method, applicable to an endoscopic image correction system comprising an endoscopic image retrieving device, a processing device and a display device, the processing device being communicatively connected to the endoscopic image retrieving device and the display device, the endoscopic image correction method comprising the steps of: retrieving, by the endoscopic image retrieving device, a first image at a first time and a second image at a second time, the first image being associated with a first image picture-taking angle and a first image display angle, and the second image being associated with a second image picture-taking angle; determining, by the processing device, a first angular difference between the first image picture-taking angle and the second image picture-taking angle; calculating a second image display angle according to the first image display angle and the first angular difference and associating the second image display angle with the second image, by the processing device; displaying, by the display device, the first image at the first image display angle; and displaying, by the display device, the second image at the second image display angle.

In a preferred embodiment of the disclosure, the second image follows the first image.

In a preferred embodiment of the disclosure, a second angular difference is defined between the first image display angle and the second image display angle and is equal to the first angular difference.

In a preferred embodiment of the disclosure, the endoscopic image correction method further comprises the step of: sensing, by a position sensor of the endoscopic image correction system, the first image picture-taking angle at the first time and the second image picture-taking angle at the second time, wherein the position sensor is communicatively connected to the processing device.

In a preferred embodiment of the disclosure, the position sensor is a G-sensor.

In a preferred embodiment of the disclosure, the processing device determines the first angular difference according to the first image picture-taking angle and the second image picture-taking angle.

In a preferred embodiment of the disclosure, the first image has a first feature region at a first position, and the second image has a second feature region at a second position, with the second feature region corresponding in position to the first feature region, wherein the processing device determines the first angular difference according to the first position and the second position.

The aforesaid aspects and other aspects of the disclosure are illustrated by non-restrictive, specific embodiments, depicted by accompanying drawings, and described below.

BRIEF DESCRIPTION OF THE DRAWINGS

FIG. 5 is a schematic view of a process flow of an endoscopic image correction method in a specific embodiment of the disclosure.

DETAILED DESCRIPTION OF THE EMBODIMENTS

Figure 1:
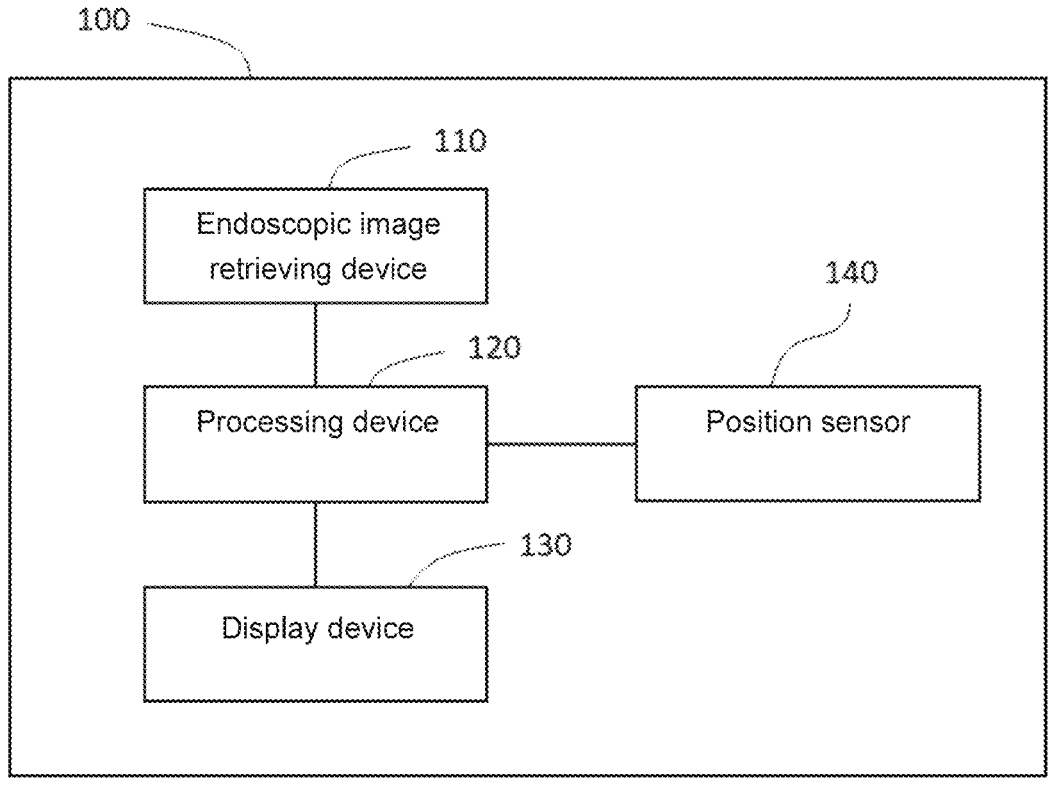
FIG. 1 is a block diagram of an endoscopic image correction system in a specific embodiment of the disclosure.

Referring to FIG. 1, there is shown a block diagram of an endoscopic image correction system in a specific embodiment of the disclosure. In the embodiment illustrated by FIG. 1, an endoscopic image correction system 100 comprises an endoscopic image retrieving device 110, processing device 120, display device 130 and position sensor 140. The processing device 120 is communicatively connected to the endoscopic image retrieving device 110, display device 130 and position sensor 140. In a specific embodiment, the position sensor 140 is connected to the endoscopic image retrieving device 110. In a specific embodiment, the position sensor 140 is communicatively connected to the processing device 120 through the endoscopic image retrieving device 110. In a specific embodiment, the position sensor 140 is a G-sensor, such as an accelerometer. In a specific embodiment, the processing device comprises one or more processors and is implemented through hardware-software synergy.

In the embodiment illustrated by FIG. 1, the endoscopic image retrieving device 110 retrieves a first image at a first time and retrieves a second image at a second time. The first image is associated with the first image picture-taking angle and the first image display angle. The second image is associated with the second image picture-taking angle. The position sensor 140 senses the first image picture-taking angle at the first time and senses the second image picture-taking angle at the second time.

In an embodiment illustrated by FIG. 1, the processing device 120 determines a first angular difference between the first image picture-taking angle and the second image picture-taking angle according to the first image picture-taking angle and the second image picture-taking angle sensed by the position sensor 140. Then, the processing device 120 calculates a second image display angle according to the first image display angle and the first angular difference. After that, the processing device 120 associates the second image display angle with the second image. Thus, the display device 130 displays the first image at the first image display angle and displays the second image at the second image display angle. In a specific embodiment, a second angular difference is defined between the first image display angle and the second image display angle. The second angular difference is equal to the first angular difference. In a specific embodiment, the display device 130 displays the first image and then displays the second image when displaying the first image and the second image, so as to create continuous, dynamic images from the first image and the second image.

Figure 2:
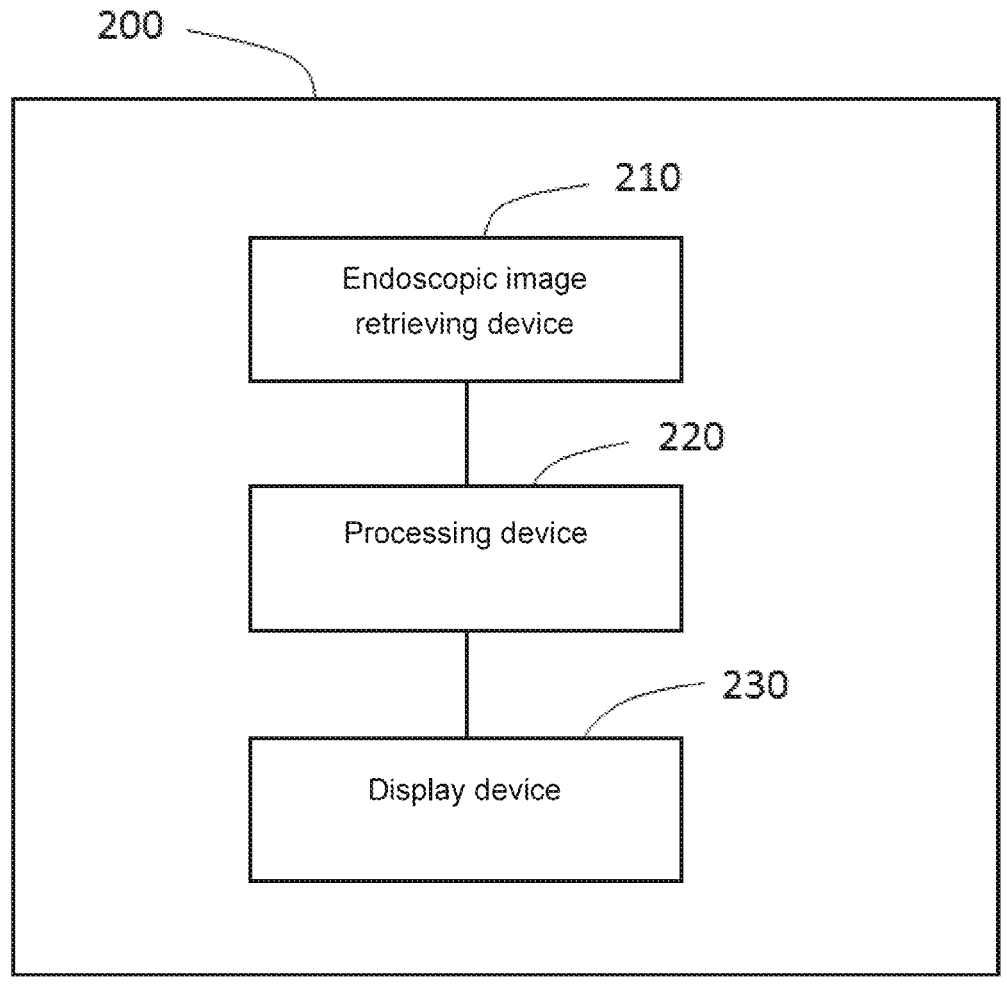
FIG. 2 is a block diagram of the endoscopic image correction system in a specific embodiment of the disclosure.

Referring to FIG. 2, there is shown a block diagram of the endoscopic image correction system in a specific embodiment of the disclosure. In the embodiment illustrated by FIG. 2, an endoscopic image correction system 200 comprises an endoscopic image retrieving device 210, processing device 220 and display device 230. The processing device 220 is communicatively connected to the endoscopic image retrieving device 210 and the display device 230. In a specific embodiment, the processing device comprises one or more processors and is implemented through hardware-software synergy.

In the embodiment illustrated by FIG. 2, the endoscopic image retrieving device 210 retrieves a first image at a first time and retrieves a second image at a second time. The first image is associated with the first image picture-taking angle and the first image display angle. The second image is associated with the second image picture-taking angle. The first image has a first feature region at a first position, and the second image has a second feature region at a second position. The second feature region corresponds in position to the first feature region. The first position is located on the first image. The second position is located on the second image.

In the embodiment illustrated by FIG. 2, the processing device 220 determines a first angular difference between the first image picture-taking angle and the second image picture-taking angle according to the first position on the first image and the second position on the second image. Then, the processing device 220 calculates a second image display angle according to the first image display angle and the first angular difference. After that, the processing device 220 associates the second image display angle with the second image Thus, the display device 230 displays the first image at the first image display angle and displays the second image at the second image display angle. In a specific embodiment, there is a second angular difference between the first image display angle and the second image display angle. The second angular difference is equal to the first angular difference. In a specific embodiment, the display device 230 displays the first image and then displays the second image when displaying the first image and the second image, so as to create continuous, dynamic images from the first image and the second image.

Figure 3A:
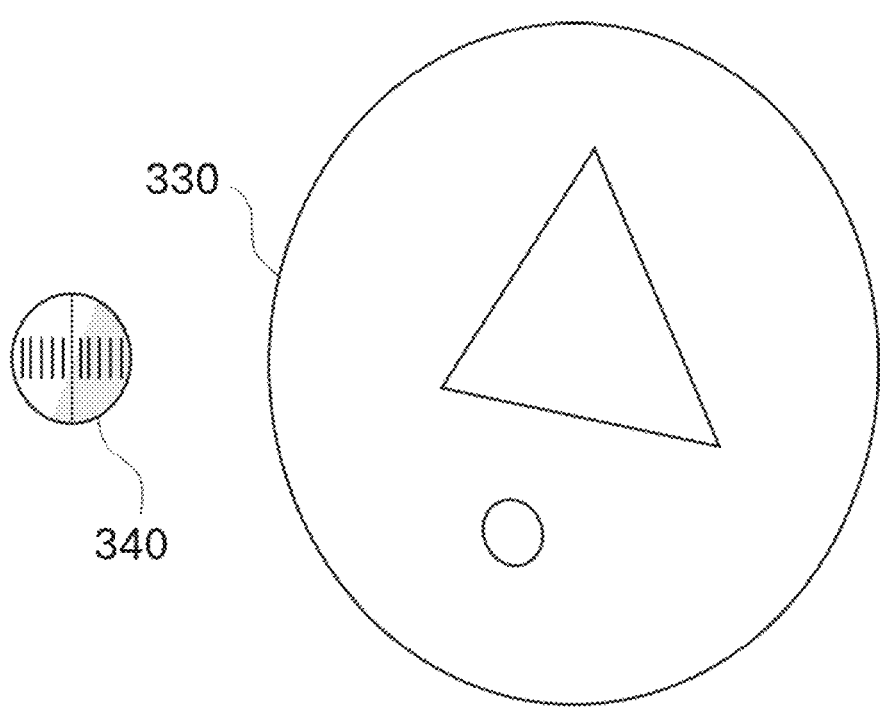
FIG. 3A is a schematic view of a first image and a second image in a specific embodiment.
Figure 3A:
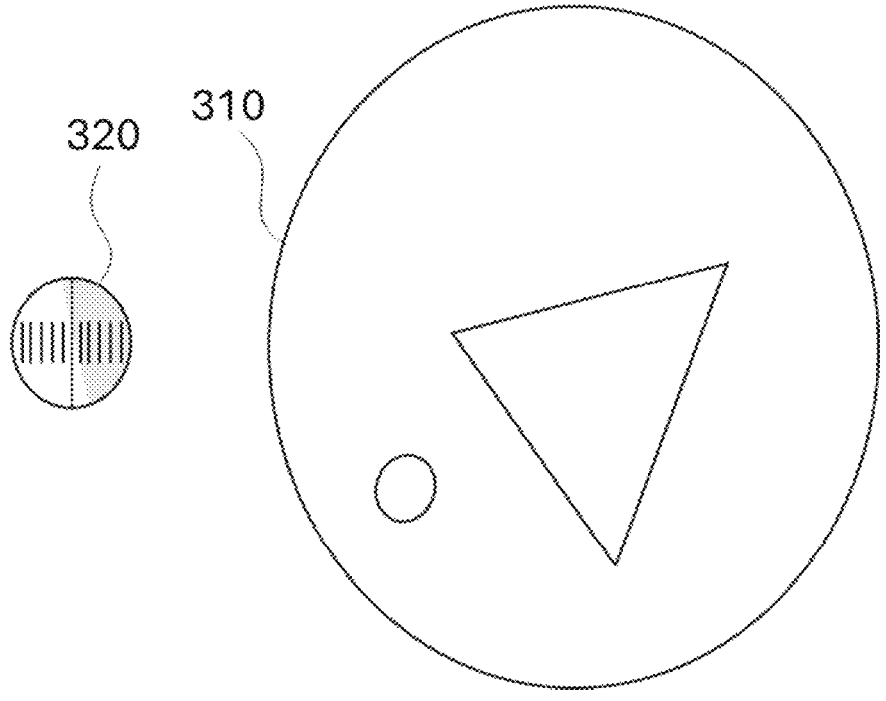

Referring to FIG. 3A, there is shown a schematic view of a first image and a second image in a specific embodiment. In the embodiment illustrated by FIG. 3A, when the endoscopic image retrieving device retrieves a first image 310, the position sensor senses that the first image picture-taking angle 320 is 10 degrees. When the endoscopic image retrieving device retrieves a second image 330, the position sensor senses that the second image picture-taking angle 340 is –15 degrees. Thus, the processing device determines that the first angular difference between the first image picture-taking angle 320 and the second image picture-taking angle 340 is 25 degrees (10 degrees–(–15 degrees)=25 degrees) according to the first image picture-taking angle 320 and the second image picture-taking angle 340 sensed by the position sensor.

Figure 3B:
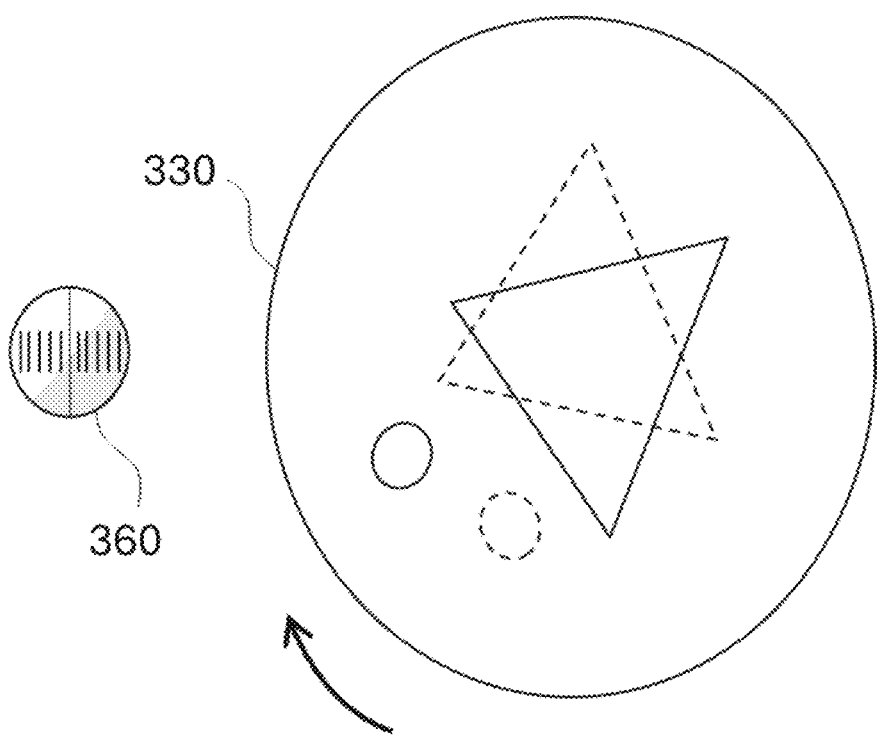
FIG. 3B is a schematic view of the first image and the second image in a specific embodiment.
Figure 3B:
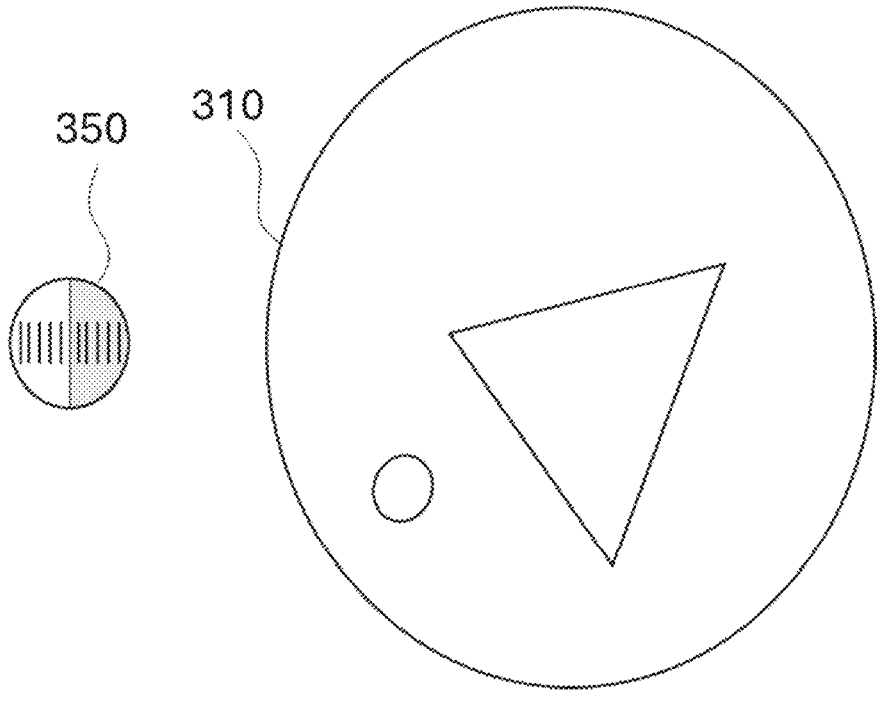

Referring to FIG. 3B, there is shown a schematic view of the first image and the second image in a specific embodiment. In the same way as what is shown in FIG. 3A, the position sensor senses that the first image picture-taking angle 320 is 10 degrees, and that the second image picture-taking angle 340 is –15 degrees, thereby allowing the processing device to determine that the first angular difference is 25 degrees. Then, as shown in FIG. 3B, the display device displays the first image 310 at the first image display angle 350 of 0 degree (i.e., displays the first image 310 at the original picture-taking viewing angle without adjusting the display angle of the first image 310). At this point in time, the display device displays the second image 330 at the second image display angle 360 of −25 degrees to preclude a difference in a viewing angle between the first image 310 and the ensuing second image 330. The second angular difference between the first image display angle 350 and the second image display angle 360 is 25 degrees (0 degree−(−25) degrees=25 degrees) and thus is equal to the first angular difference. The first image display angle is not necessarily equal to 0 degree but is subject to changes as needed. However, regardless of the changes made to the first image display angle, the second angular difference between the first image display angle and the second image display angle must be equal to the first angular difference.

Figure 4A:
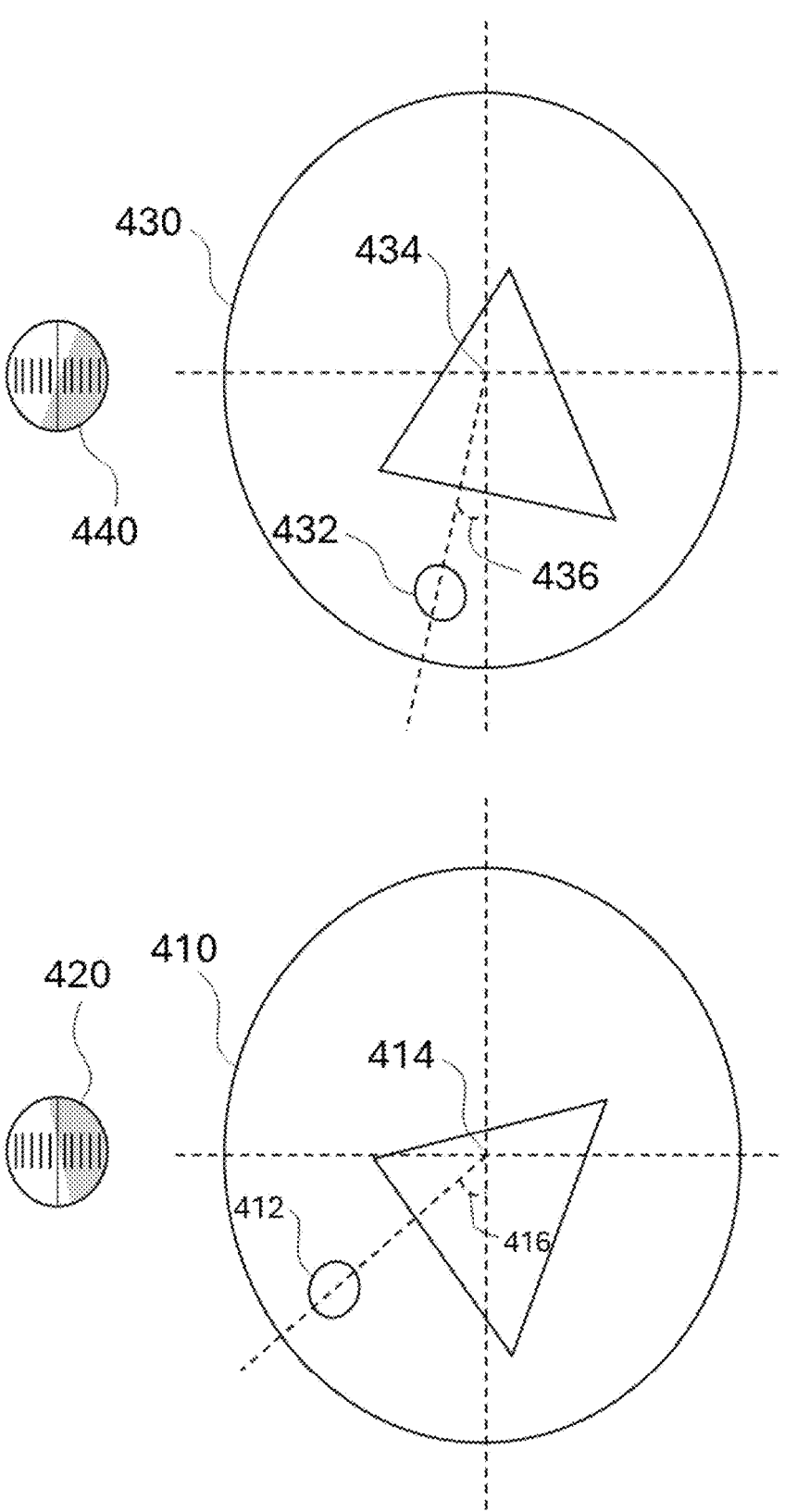
FIG. 4A is a schematic view of a first image and a second image in a specific embodiment.

Referring to FIG. 4A, there is shown a schematic view of a first image and a second image in a specific embodiment. In the embodiment illustrated by FIG. 4A, a first image 410 has a first feature region 412 at a first position, and a second image 430 has a second feature region 432 at a second position. The first feature region 412 on the first image 410 corresponds in position to the second feature region 432 on the second image 430. Thus, the first feature region 412 and the second feature region 432 correspond in position to the same object. The processing device of the endoscopic image correction system calculates a first relative angle 416 according to the first position and a first center position 414 of the first image 410 and calculates a second relative angle 436 according to the second position and a second center position 434 of the second image 430. Then, the processing device calculates a third angular difference between the first relative angle 416 and the second relative angle 436. The third angular difference is equal to the first angular difference between the first image picture-taking angle 420 and the second image picture-taking angle 440.

Figure 4B:
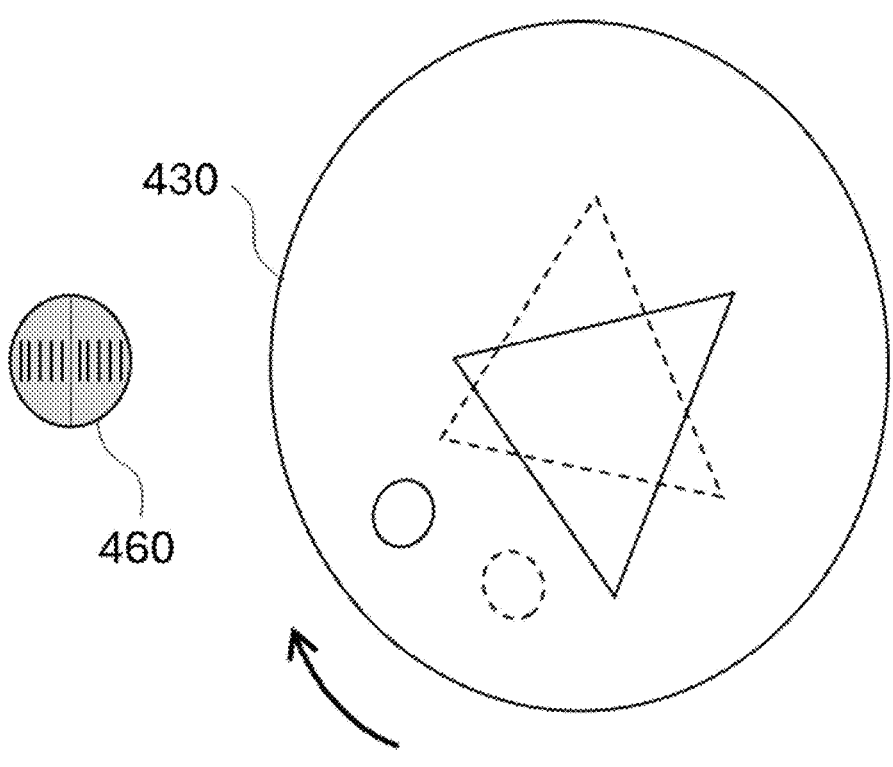
FIG. 4B is a schematic view of the first image and the second image in a specific embodiment.
Figure 4B:
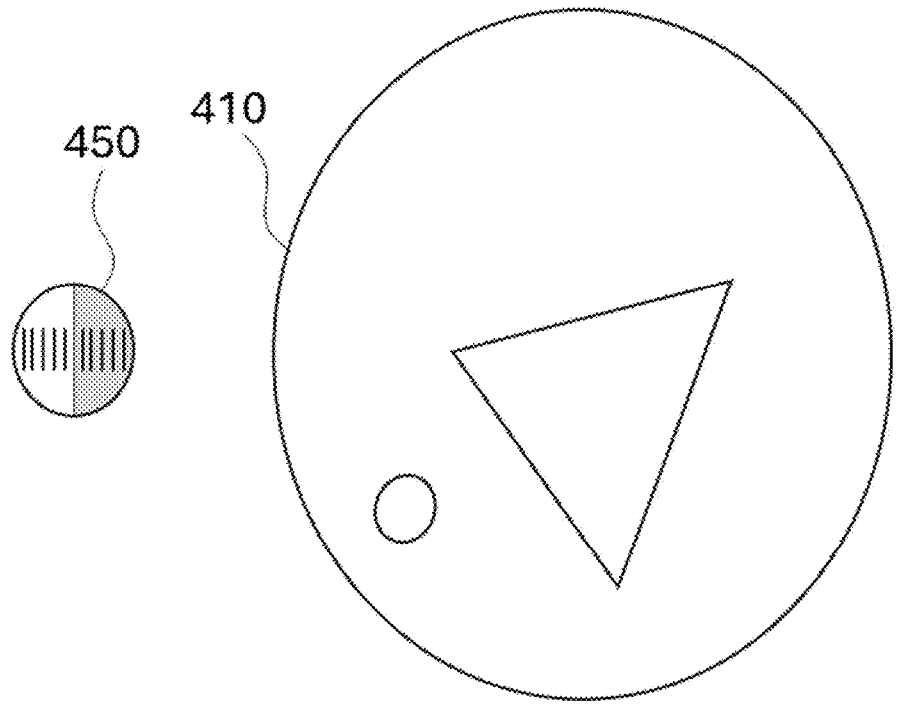

Referring to FIG. 4B, there is shown a schematic view of the first image and the second image in a specific embodiment. As shown in FIG. 4B, the display device displays the first image 410 at a first image display angle 450 of 0 degree (i.e., displays the first image 410 at the original picture-taking viewing angle without adjusting the display angle of the first image 410). At this point in time, to preclude a difference in a viewing angle between the first image 410 and the ensuing second image 430, the processing device calculates a second image display angle 460 by subtracting the first angular difference from the first image display angle 450, and the display device displays the second image 430 at the second image display angle 460. The second angular difference between the first image display angle 350 and the second image display angle 360 is equal to the first angular difference. The first image display angle is not necessarily equal to 0 degree but is subject to changes as needed. However, regardless of the changes made to the first image display angle, the second angular difference between the first image display angle and the second image display angle must be equal to the first angular difference.

FIG. 4A and FIG. 4B serve illustrative purposes only. The determination of the first angular difference or second image display angle by the processing device is not necessarily achieved with the method of the disclosure. In an alternative embodiment, the determination of the first angular difference, second angular difference or second image display angle may also be achieved by rotating the second image in such a way that the second position on the second image corresponds in position to the first position on the first image. The angle by which the second image rotates is equal to the second angular difference between the first image display angle and the second image display angle, whereas the second angular difference is actually equal to the first angular difference.

Referring to FIG. 5, there is shown a schematic view of a process flow of an endoscopic image correction method in a specific embodiment of the disclosure. In the embodiment illustrated by FIG. 5, an endoscopic image correction method 500 is applicable to an endoscopic image correction system. The endoscopic image correction system comprises an endoscopic image retrieving device, processing device and display device. The processing device is communicatively connected to the endoscopic image retrieving device and the display device. The endoscopic image correction method 500 starts with step 510 which involves retrieving, by the endoscopic image retrieving device, a first image at a first time and a second image at a second time. The first image is associated with the first image picture-taking angle and the first image display angle. The second image is associated with the second image picture-taking angle. In a specific embodiment, the second image follows the first image. Then, step 520 entails determining, by the processing device, a first angular difference between the first image picture-taking angle and the second image picture-taking angle. Then, step 530 entails calculating a second image display angle according to the first image display angle and the first angular difference and associating the second image display angle with the second image, by the processing device. In a specific embodiment, a second angular difference is defined between the first image display angle and the second image display angle and is equal to the first angular difference. Then, step 540 entails displaying, by the display device, the first image at the first image display angle. Finally, step 550 entails displaying, by the display device, the second image at the second image display angle.

In a specific embodiment, the endoscopic image correction method 500 further comprises the step of sensing, by a position sensor of the endoscopic image correction system, the first image picture-taking angle at the first time and the second image picture-taking angle at the second time. The position sensor is communicatively connected to the processing device. In a specific embodiment, the processing device determines the first angular difference according to the first image picture-taking angle and the second image picture-taking angle sensed by the position sensor. In a specific embodiment, the first image has a first feature region at a first position, and the second image has a second feature region at a second position, with the second feature region corresponding in position to the first feature region. The first position is located on the first image. The second position is located on the second image. The processing device determines the first angular difference according to the first position and the second position.

The endoscopic image correction system and method of the disclosure are depicted by drawings and described above. Specific embodiments of the disclosure merely serve illustrative purposes. Various changes made to the specific embodiments without departing from the spirit and claims of the disclosure must be deemed falling within the scope of the claims of the disclosure. Accordingly, the spirit and scope of the disclosure should be defined by the appended claims, and the specific embodiments are not restrictive of the disclosure.

What is claimed is:

1. An endoscopic image correction system, comprising:
an endoscopic image retrieving device for retrieving a first image at a first time and a second image at a second time, the first image being associated with a first image picture-taking angle and a first image display angle, and the second image being associated with a second image picture-taking angle;
a processing device for determining a first angular difference between the first image picture-taking angle and the second image picture-taking angle, calculating a second image display angle according to the first image display angle and the first angular difference, and associating the second image display angle with the second image;
a display device for displaying the first image at the first image display angle and the second image at the second image display angle, and
a position sensor coupled to the endoscopic image retrieving device for sensing the first image picture-taking angle at the first time and sensing the second image picture-taking angle at the second time, wherein the position sensor is communicatively coupled to the processing device;
wherein the processing device is communicatively connected to the endoscopic image retrieving device and the display device; and
wherein a second angular difference is defined between the first image display angle and the second image display angle and is equal to the first angular difference.

2. The endoscopic image correction system of claim 1, wherein the second image follows the first image.

3. The endoscopic image correction system of claim 1, wherein the position sensor is a G-sensor.

4. The endoscopic image correction system of claim 1, wherein the processing device determines the first angular difference according to the first image picture-taking angle and the second image picture-taking angle.

5. The endoscopic image correction system of claim 1, wherein the first image has a first feature region at a first position, and the second image has a second feature region at a second position, with the second feature region corresponding in position to the first feature region, wherein the processing device determines the first angular difference according to the first position and the second position.

6. An endoscopic image correction method, applicable to an endoscopic image correction system comprising an endoscopic image retrieving device, a processing device and a display device, the processing device being communicatively connected to the endoscopic image retrieving device and the display device, the endoscopic image correction method comprising the steps of:
retrieving, by the endoscopic image retrieving device, a first image at a first time and a second image at a second time, the first image being associated with a first image picture-taking angle and a first image display angle, and the second image being associated with a second image picture-taking angle;
determining, by the processing device, a first angular difference between the first image picture-taking angle and the second image picture-taking angle;
calculating a second image display angle according to the first image display angle and the first angular difference and associating the second image display angle with the second image, by the processing device;
sensing, by a position sensor of the endoscopic image correction system, the first image picture-taking angle at the first time and the second image picture-taking angle at the second time, wherein the position sensor is coupled to the endoscopic image retrieving device and further wherein the position sensor is communicatively coupled to the processing device;
displaying, by the display device, the first image at the first image display angle; and
displaying, by the display device, the second image at the second image display angle;
wherein a second angular difference is defined between the first image display angle and the second image display angle and is equal to the first angular difference.

7. The endoscopic image correction method of claim 6, wherein the second image follows the first image.

8. The endoscopic image correction method of claim 6, wherein the position sensor is a G-sensor.

9. The endoscopic image correction method of claim 6, wherein the processing device determines the first angular difference according to the first image picture-taking angle and the second image picture-taking angle.

10. The endoscopic image correction method of claim 6, wherein the first image has a first feature region at a first position, and the second image has a second feature region at a second position, with the second feature region corresponding in position to the first feature region, wherein the processing device determines the first angular difference according to the first position and the second position.

* * * * *